(12) United States Patent
Takenaka et al.

(10) Patent No.: US 10,815,268 B2
(45) Date of Patent: Oct. 27, 2020

(54) 15-OXOSTEROID COMPOUND AND PROCESS FOR PRODUCING THE SAME

(71) Applicant: ASKA Pharmaceutical Co., Ltd., Tokyo (JP)

(72) Inventors: Yosuke Takenaka, Kanagawa (JP); Norihito Isomura, Kanagawa (JP); Akira Asagarasu, Kanagawa (JP); Hiroshi Uchida, Kanagawa (JP)

(73) Assignee: ASKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/481,970

(22) PCT Filed: Feb. 8, 2018

(86) PCT No.: PCT/JP2018/004295
§ 371 (c)(1),
(2) Date: Jul. 30, 2019

(87) PCT Pub. No.: WO2018/147345
PCT Pub. Date: Aug. 16, 2018

(65) Prior Publication Data
US 2019/0389900 A1    Dec. 26, 2019

(30) Foreign Application Priority Data
Feb. 10, 2017 (JP) .................. 2017-023569

(51) Int. Cl.
*C07J 73/00*    (2006.01)
*C07J 75/00*    (2006.01)

(52) U.S. Cl.
CPC .................... *C07J 73/003* (2013.01)

(58) Field of Classification Search
CPC ................ C07J 73/003; C07J 75/00
See application file for complete search history.

(56) References Cited

U.S. PATENT DOCUMENTS
2006/0211857 A1    9/2006    Burgoyne et al.

FOREIGN PATENT DOCUMENTS

| JP | 1-199993   | 8/1989 |
|----|------------|--------|
| JP | 2591640    | 3/1997 |
| JP | 2001-503732| 3/2001 |

OTHER PUBLICATIONS

International Search Report dated Mar. 27, 2018 in International Application No. PCT/JP2018/004295.
Takegawa et al., "Antiandrogen. II. Oxygenated 2-Oxapregnane Steroids", Chem. Pharm. Bull. 41(5) 870-875 (1993).
Zhao et al., "An Unexpected Oxidation of Unactivated Methylene C-H Using DIB/TBHP Protocol", Organic Letters, 2011, vol. 13, No. 16, p. 4308-4311.
Ogawa et al., "Osmiumporphyrin-Catalyzed Oxyfunctionalization and Isomerization of Natural (5β)-Bile Acids with tert-Butyl Hydroperoxide", European Journal of Organic Chemistry, 2007, No. 21, p. 3555-3563.
Jida et al., "Potential Bile Acid Metabolites. 25. Synthesis and Chemical Properties of Stereoisomeric 3α,7α,16- and 3α,7α,15-Trihydroxy-5-β-cholan-24-oic Acids[1]", Chemical & Pharmaceutical Bulletin, 2002, vol. 50, No. 10, p. 1327-1334.
International Preliminary Report on Patentability dated Aug. 13, 2019 in International Application No. PCT/JP2018/004295.

*Primary Examiner* — Brenda L Coleman
(74) *Attorney, Agent, or Firm* — Wenderoth, Lind & Ponack, L.L.P.

(57) ABSTRACT

Provided is a process for producing a compound, which has an oxo group specifically introduced on the 15-position of a steroid skeleton and which is useful as an intermediate, with a high yield without complicated steps. A compound represented by the formula (2) is allowed to react with an oxidant (e.g., a hypervalent iodine compound) and a co-oxidant (e.g., a peroxide) to produce a 15-oxosteroid compound represented by the formula (1), which is useful as an intermediate:

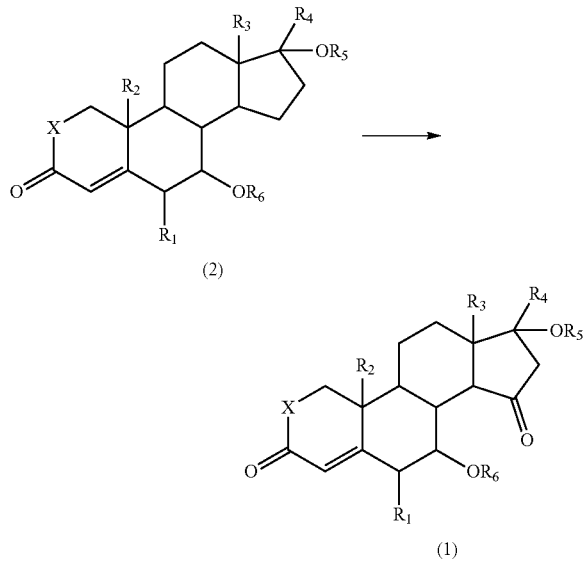

wherein $R_1$ to $R_3$ are the same or different and each represent a halogen atom, an alkyl group, a haloalkyl group, an alkoxy group, or a haloalkoxy group, $R_4$ represents a hydrogen atom, a halogen atom, an alkyl group, an alkoxy group, an acyl group, or an alkoxycarbonyl group, $R_5$ represents a hydrogen atom, an alkyl group, or an acyl group, $R_6$ represents a hydrogen atom, an alkyl group, an acyl group, or a sulfonyl group, X represents an oxygen atom (O) or a methylene group ($CH_2$).

7 Claims, No Drawings

15-OXOSTEROID COMPOUND AND PROCESS FOR PRODUCING THE SAME

TECHNICAL FIELD

The present invention relates to a 15-oxosteroid compound useful as an intermediate for preparing a compound having an oxo group introduced on the 15-position of a steroid skeleton thereof and having a pharmacological activity (for example, an antiandrogenic activity), and a process for producing the 15-oxosteroid compound.

BACKGROUND ART

Pregnane compounds (pregnane steroid compounds) having various physiological activities or pharmacological activities are prepared by introducing various functional groups or active groups to the steroid skeletons. Steroid compounds having antiandrogenic activities are used as agents for treating benign prostatic hyperplasia (prostatomegaly) or other diseases. However, complicated steps are required to introduce an oxygen-containing functional group to the 15-position of the steroid skeleton.

Japanese Patent No. 2591640 (Patent Document 1) and Chem. Pharm. Bull. 41(5) 870-875 (1993) (Nonpatent Document 1) refer to a 2-oxapregnane compound having acetoxy group introduced on the 15-position of a steroid skeleton thereof and disclose 17α-acetoxy-6-chloro-2-oxa-4,6-pregnadiene-3,15,20-trione (Compound 16 of Chart 2 of the Nonpatent Document 1). Reaction Formula B of the Patent Document 1 and Chart 2 of the Nonpatent Document 1 disclose that (a) 17-hydroxy-6-chloro-2-oxa-4,6-pregnadiene-3,20-dione (Compound 8) is dehydrated with phosphorus oxychloride to produce 6-chloro-2-oxa-4,6,16-pregnatriene-3,20-dione (Compound 9), (b) the produced 16-dehydro compound is oxidized to produce 6-chloro-17α-hydroxy-2-oxa-4,6,15-pregnatriene-3,20-dione (Compound 10), (c) the produced 15-dehydro compound is subjected to an addition reaction with N-bromoacetamide (NBA), for giving 15β-acetoxy-16α-bromo-6-chloro-17α-hydroxy-2-oxa-4,6-pregnadiene-3,20-dione (Compound 12: bromo compound).

Unfortunately, these processes, in which acetoxy group is introduced on the 15-position of the steroid skeleton through three steps (the dehydration step, the oxidation step, and the addition step), significantly lower the yield of the pregnane compound. Further, because the addition reaction with N-bromoacetamide introduces a bromine atom on the 16-position of the steroid skeleton, removal of the bromine atom requires debromination of Compound 12.

In particular, more complicated steps are required to obtain the 2-oxapregnane compound (Compound 16) in which the oxo group is introduced on the 15-position of a steroid skeleton thereof. Specifically, it is necessary to debrominate Compound 12 to produce a 17-hydroxy compound (Compound 13) (debromination step), to acetylate the 17-hydroxy compound to produce a 15β,17-diacetoxy compound (Compound 14) (acetylation step), to hydrolyze the diacetoxy compound to produce a 15β-hydroxy compound (hydrolyzation step), and to oxidize the produced 15β-hydroxy compound to form a 15-oxo compound (a 3,15,20-trione compound of Compound 16) (oxidation step). Thus, the 2-oxapregnane compound in which the oxo group is introduced on the 15-position of the steroid skeleton cannot be produced with a high yield by a simple method.

Org. Lett. Vol. 13, No. 16 4308-4311 (2011) (Nonpatent Document 2) discloses oxidation of an unreactive, remote and isolated methylene group of a cycloalkyl or alkyl ester or amide with the use of diacetoxyiodobenzene (DIB) and t-butyl hydroperoxide (TBHP). The Nonpatent Document 2 discloses that cyclopentyl acetate is oxidized to give 3-oxo-cyclopentyl acetate with a yield of 32% and that cyclohexyl acetate is oxidized to give 3-oxocyclohexyl acetate and 4-oxocyclohexyl acetate with a total yield of 52%.

CITATION LIST

Patent Literature

Patent Document 1: Japanese Patent No. 2591640 (Claims, Reaction Formula B, and Example 3)

Nonpatent Literature

Nonpatent Document 1: Chem. Pharm. Bull. 41(5) 870-875 (1993) (Chart 2)

Nonpatent Document 2: Org. Lett. Vol. 13, No. 16 4308-4311 (2011) (Table 2)

SUMMARY OF INVENTION

Technical Problem

It is therefore an object of the present invention to provide a compound having an oxo group specifically introduced on the 15-position of a steroid skeleton thereof, and a process for efficiently producing such a compound without complicated steps.

Another object of the present invention is to provide a compound having an oxo group on the 15-position of a steroid skeleton thereof, and a process for producing the compound with a high yield by one or single step (or one-pot reaction).

It is still another object of the present invention to provide a steroid compound useful for preparing a compound having a high pharmacological activity (for example, an antiandrogenic activity), and a process for producing the steroid compound.

Solution to Problem

The inventors of the present invention made intensive studies modification of a steroid skeleton to achieve the above objects and finally found that a compound having a substituent (such as hydroxy group) at the 7-position of a steroid skeleton thereof is specifically oxidized at the 15-position of the steroid skeleton to introduce an oxo group and that use of such a compound having the oxo group introduced on the 15-position of the steroid skeleton as an intermediate enables easy preparation of a compound having a high pharmacological activity (for example, an antiandrogenic activity). The present invention was accomplished based on the above findings.

That is, the present invention provides a 15-oxosteroid compound represented by the following formula (1). Incidentally, respective positions of the steroid skeleton in the following formula (1) are denoted by positional numbers.

[Chem. 1]

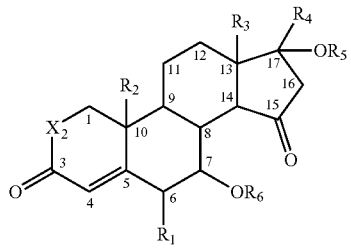

(1)

In the formula, $R_1$ to $R_3$ are the same or different and each represent a halogen atom, an alkyl group, a haloalkyl group, an alkoxy group, or a haloalkoxy group, $R_4$ represents a hydrogen atom, a halogen atom, an alkyl group, an alkoxy group, an acyl group, or an alkoxycarbonyl group, $R_5$ represents a hydrogen atom, an alkyl group, or an acyl group, $R_6$ represents a hydrogen atom, an alkyl group, an acyl group, or a sulfonyl group, and X represents an oxygen atom (O) or a methylene group ($CH_2$).

$R_1$ may be a halogen atom, $R_2$ to $R_3$ are the same or different and may be an alkyl group or a haloalkyl group, $R_4$ and $R_5$ may be the same or a different acyl group, $R_6$ may be a hydrogen atom, an acyl group, or a sulfonyl group, and X may be an oxygen atom (O).

The 15-oxosteroid compound represented by the above formula (1) may be a racemate or an optically active substance (or an optical isomer) represented, for example, by the following formula (1a):

[Chem. 2]

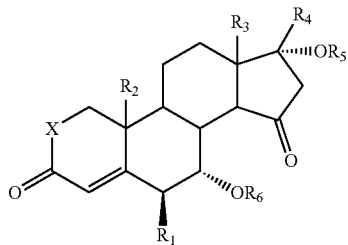

(1a)

wherein $R_1$ to $R_6$ and X have the same meanings as defined above.

The present invention also provides a process for producing the 15-oxosteroid compound. According to this process, the compound represented by the above formula (1) may be prepared by oxidizing a compound represented by the following formula (2) to introduce an oxo group on the 15-position of the steroid skeleton.

[Chem. 3]

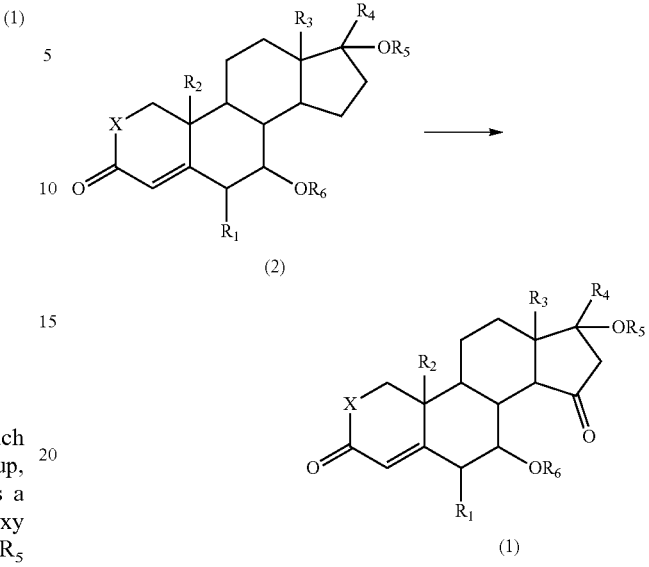

In the formulae, $R_1$ to $R_6$ and X have the same meanings as defined above.

For example, the 15-oxosteroid compound represented by the above formula (1) may be produced by oxidizing the compound represented by the formula (2) with an oxidant and a co-oxidant (co-oxidizing agent).

In this process, an optically active compound represented by the formula (2a) may be used as the compound represented by the formula (2) to produce the optical isomer represented by the above formula (1a) while maintaining the configuration thereof.

[Chem. 4]

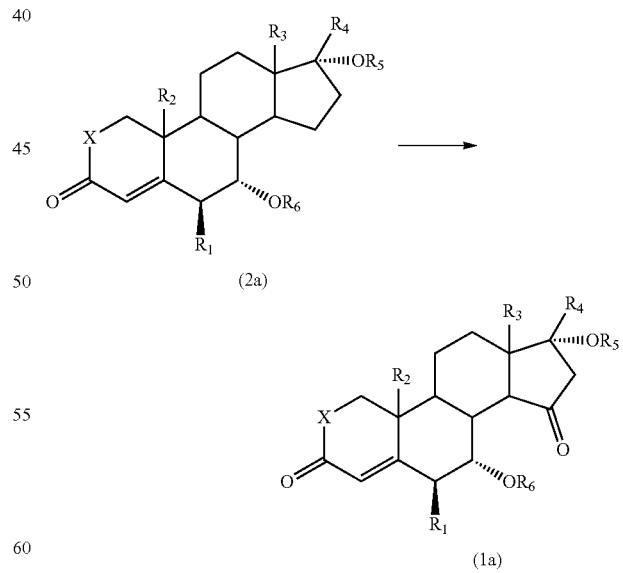

In the formulae, $R_1$ to $R_6$ and X have the same meanings as defined above.

In this process, the oxidant may contain, for example, a hypervalent iodine compound. The co-oxidant may contain a peroxide and/or a peroxy acid. In the oxidation with the oxidant and the co-oxidant, the reaction may be carried out in the coexistence of a coexisting substance such as an acid, a base, or a salt. The coexisting substance may positively coexist with the oxidant and the co-oxidant in the reaction, and the coexisting substance may be added to the reaction system in advance before the addition of the oxidant and the co-oxidant to the reaction system or may be added after the addition of the oxidant and the co-oxidant to the reaction system. More specifically, the compound represented by the above formula (1) may be produced by allowing the compound represented by the above formula (2) to react with the hypervalent iodine compound and the peroxide in the presence of a strong acid in a solvent (for example, a solvent inert or inactive to the reaction), then adding an alkali metal carbonate to the reaction system and continuing the reaction.

Advantageous Effects of Invention

According to the present invention, the compound having the oxo group specifically introduced on the 15-position of the steroid skeleton is simply and efficiently producible through the specific intermediate (the compound (2)) without complicated steps. In particular, the compound having the oxo group on the 15-position of the steroid skeleton is producible with a high yield by one or single step (or one-pot reaction). Furthermore, use of the compound having the oxo group introduced on the 15-position of the steroid skeleton as an intermediate enables simple production of a compound having a high pharmacological activity (for example, an antiandrogenic activity) with a reduced or small number of steps.

DESCRIPTION OF EMBODIMENTS

[15-Oxosteroid Compound]

A compound represented by the above formula (1) is a novel compound and is useful for producing a compound having a high pharmacological activity (for example, an antiandrogenic activity).

In the above formula (1), a halogen atom represented by each of $R_1$ to $R_4$ may include a fluorine atom, a chlorine atom, a bromine atom, and an iodine atom. The halogen atom may practically be a fluorine atom, a chlorine atom, or a bromine atom, particularly a fluorine atom or a chlorine atom.

As examples of an alkyl group represented by each of $R_1$ to $R_6$, there may be mentioned a straight-chain or branched-chain $C_{1-12}$alkyl group such as methyl group, ethyl group, propyl group, isopropyl group, butyl group, isobutyl group, s-butyl group, t-butyl group, pentyl group, isopentyl group, hexyl group, or octyl group. The alkyl group is usually a straight-chain or branched-chain $C_{1-6}$alkyl group, preferably a straight-chain or branched-chain $C_{1-4}$alkyl group, and more preferably a straight-chain or branched-chain $C_{1-3}$alkyl group.

An alkoxy group represented by each of $R_1$ to $R_4$ may include an alkoxy group corresponding to the alkyl group, for example, a straight-chain or branched-chain $C_{1-12}$alkoxy group such as methoxy group, ethoxy group, propoxy group, isopropoxy group, butoxy group, or t-butoxy group. The alkoxy group is usually a straight-chain or branched-chain $C_{1-6}$alkoxy group, preferably a straight-chain or branched-chain $C_{1-4}$alkoxy group, and more preferably a straight-chain or branched-chain $C_{1-3}$alkoxy group.

As examples of a halogen atom in a haloalkyl group and a haloalkoxy group represented by each of $R_1$ to $R_3$, there may be mentioned the halogen atom exemplified in the above. The halogen atom is usually a fluorine atom, a chlorine atom, or a bromine atom, particularly a fluorine atom or a chlorine atom. Examples of the haloalkyl group may include a straight-chain or branched-chain haloC$_{1-12}$alkyl group such as chloromethyl group, trichloromethyl group, fluoromethyl group, trifluoromethyl group, 2,2,2-trichloroethyl group, perchloroethyl group, 2,2,2-trifluoroethyl group, perfluoroethyl group, or perfluoroisopropyl group. The haloalkyl group is usually a straight-chain or branched-chain haloC$_{1-6}$alkyl group such as trichloromethyl group or trifluoromethyl group, preferably a haloC$_{1-4}$alkyl group, and more preferably a haloC$_{1-3}$alkyl group.

As examples of the haloalkoxy group represented by each of $R_1$ to $R_3$, there may be mentioned a haloalkoxy group corresponding to the haloalkyl group, for example, a straight-chain or branched-chain haloC$_{1-12}$alkoxy group such as trichloromethoxy group, trifluoromethoxy group, perchloroethoxy group, perfluoroethoxy group, or perfluoropropoxy group. The haloalkoxy group is usually a straight-chain or branched-chain haloC$_{1-6}$alkoxy group such as trichloromethoxy group or trifluoromethoxy group, preferably a haloC$_{1-4}$alkoxy group, and more preferably a haloC$_{1-3}$alkoxy group.

An acyl group represented by each of $R_4$, $R_5$, and $R_6$ may include, for example, formyl group; a straight-chain or branched-chain $C_{1-12}$alkyl-carbonyl group such as acetyl group, propionyl group, butyryl group, isobutyryl group, t-butyryl group, pentanoyl group (valeryl group), or hexanoyl group; a $C_{3-10}$cycloalkyl-carbonyl group such as cyclohexylcarbonyl group; a $C_{6-12}$aryl-carbonyl group which may have a substituent (such as a $C_{1-4}$alkyl group, a halogen atom, or a nitro group), e.g., benzoyl group, toluoyl group, or naphthoyl group; and a heterocyclic acyl group having at least one hetero atom selected from an oxygen atom, a sulfur atom, and a nitrogen atom (such as furoyl group, nicotinoyl group, or isonicotinoyl group). The acyl group is usually an alkylcarbonyl group, for example, a straight-chain or branched-chain $C_{1-6}$alkyl-carbonyl group, preferably a $C_{2-4}$alkyl-carbonyl group, and more preferably a $C_{2-3}$alkyl-carbonyl group.

An alkoxycarbonyl group represented by $R_4$ may include, for example, a straight-chain or branched-chain $C_{1-12}$alkoxy-carbonyl group such as methoxycarbonyl group, ethoxycarbonyl group, propoxycarbonyl group, isopropoxycarbonyl group, butoxycarbonyl group, t-butoxycarbonyl group, or hexyloxycarbonyl group. The alkoxycarbonyl group is usually a straight-chain or branched-chain $C_{1-6}$alkoxy-carbonyl group, preferably a $C_{1-4}$alkoxy-carbonyl group, and more preferably a $C_{1-3}$alkoxy-carbonyl group.

As examples of a sulfonyl group represented by $R_6$, there may be mentioned a $C_{1-6}$alkanesulfonyl group such as methanesulfonyl group, ethanesulfonyl group, or t-butanesulfonyl group, and a $C_{6-12}$arenesulfonyl group which may have a substituent (such as a $C_{1-4}$alkyl group, a halogen atom, or a nitro group), e.g., benzenesulfonyl group or toluenesulfonyl group.

X may be either an oxygen atom (O) or a methylene group ($CH_2$).

In the 15-oxosteroid compound represented by the above formula (1), $R_1$ may practically be a halogen atom (e.g., a fluorine atom or a chlorine atom) and $R_2$ and $R_3$ may practically be the same or different and each represent an alkyl group (e.g., a straight-chain or branched-chain $C_{1-4}$alkyl group) or a haloalkyl group (e.g., a straight-chain or branched-chain $C_{1-4}$alkoxy group). Moreover, in practical cases, $R_4$ and $R_5$ may be the same or a different acyl group, for example, an alkylcarbonyl group (e.g., a straight-chain or branched-chain $C_{1-4}$alkyl-carbonyl group), $R_6$ may be a hydrogen atom or an acyl group (e.g., an alkylcarbonyl group such as a straight-chain or branched-chain $C_{1-4}$alkyl-carbonyl group), and X may be an oxygen atom (O).

The 15-oxosteroid compound represented by the formula (1) may be a racemate or may be an optical isomer. A preferred 15-oxosteroid compound includes an optically active substance (an optical isomer) represented by the following formula (1a):

[Chem. 5]

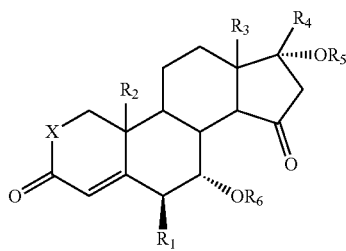

(1a)

wherein $R_1$ to $R_6$ and X have the same meanings as defined above.

The 15-oxosteroid compound represented by the above formula (1) or (1a) may have a physiological activity or a pharmacological activity. Use of the 15-oxosteroid compound of the present invention as an intermediate provides a compound having a physiological activity or a pharmacological activity simply with a high yield. For example, in the formula (1) or (1a), the group —$OR_6$ on the 7-position of the steroid skeleton may be eliminated with a usual method to prepare a compound which is represented by the following formula (3) or (3a) and which is described in the Nonpatent Document 1 (such as Compound

[Chem. 6]

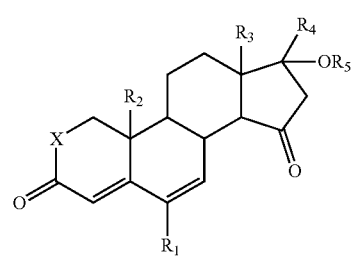

(3)

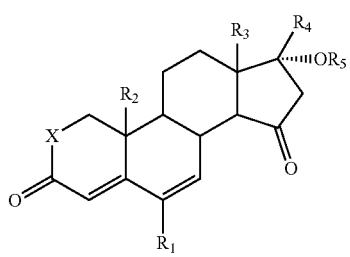

(3a)

wherein $R_1$ to $R_5$ and X have the same meanings as defined above.

Concretely, for example, the compound represented by the above formula (1) in which the group —$OR_6$ is hydroxyl group may be, for example, subjected to a dehydration reaction in the presence of an eliminating agent (such as thionyl chloride, phosphorus oxychloride, or Martin sulfurane) to prepare the compound represented by the formula (3) or (3a).

Moreover, in a case where the compound has an alkoxy group as the group —$OR_6$, the alkoxy group may be converted into hydroxyl group with an action of an acid (for example, sulfuric acid, hydriodic acid, and hydrobromic acid) and subjected to the same dehydration reaction as above, thus preparing the compound represented by the formula (3) or (3a).

In a case where the compound has an acyloxy group (such as acetyloxy group) or a sulfonyloxy group as the group —$OR_6$, the group —$OR_6$ may be eliminated (or liberated) by subjecting the compound to an elimination reaction in the presence of a basic solvent or a base (e.g., an alkali metal hydroxide, an alkali metal carbonate, and an alkali metal acetate such as sodium acetate or potassium acetate).

[Process for Producing 15-Oxosteroid Compound]

The 15-oxosteroid compound represented by the above formula (1) may be prepared by oxidizing the compound represented by the following formula (2). Even in a case where the compound represented by the following formula (2a) is oxidized, the optically active substance represented by the formula (1a) may be prepared while maintaining the configuration (steric configuration).

[Chem. 7]

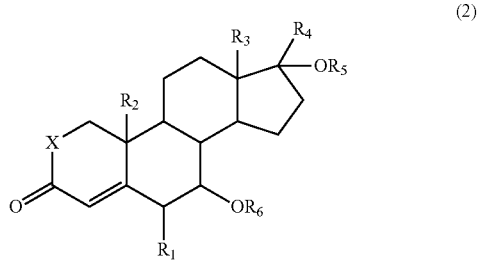

(2)

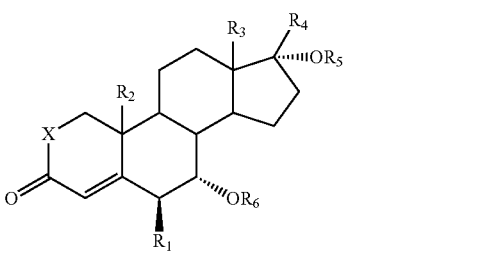

(2a)

In the formulae, $R_1$ to $R_6$ and X have the same meanings as defined above.

The compound represented by the above formula (2) or (2a) is a known substance. For example, the compound in which RE is hydroxyl group and the compound in which $R_6$ is acetyl group are described as Compound 11 and Compound 13 in Chart 2 of Chem. Pharm. Bull. 40(4), 935-941 (1992). Thus, the compound represented by the formula (2) or (2a) may be prepared in accordance with the method described in this document, or if possible, may be commercially available one.

The oxidation reaction may be carried out using an oxidant and a co-oxidant.

Examples of the oxidant may include a hypervalent iodine compound (an organic periodide or a catalyst), e.g., iodosobenzene diacetate (or iodobenzene diacetate), [bis(trifluoroacetoxy) iodo]benzene, (di-tert-butylcarbonyloxyiodo)benzene, (hydroxytosyloxyiodo)benzene (Koser reagent), (difluoroiodo)toluene, 2-iodoxybenzoic acid, 2-iodoxybenzenesulfonic acid, iodosylbenzene, and iodoxybenzene. Moreover, the oxidant may be an active species or the above-mentioned catalyst generated from an organoiodine compound in the reaction system. These oxidants may be used alone or in combination. A preferred oxidant includes iodobenzene diacetate, [bis(trifluoroacetoxy)iodo]benzene, or other oxidants.

The amount of the oxidant may be, for example, about 0.1 to 50 mol, preferably about 0.5 to 25 mol (e.g., about 1 to 20 mol), and more preferably about 2 to 10 mol (e.g., about 3 to 8 mol), relative to 1 mol of the compound represented by the formula (2).

The co-oxidant may include a peroxide, for example, hydrogen peroxide, tert-butyl hydroperoxide (TBHP), di-tert-butyl peroxide, tert-amyl hydroperoxide, di-tert-amyl peroxide, cumene hydroperoxide, dicumyl peroxide, tert-butyl cumyl peroxide, tert-butyl peroxypyvalate, benzoyl peroxide, lauroyl peroxide, and ethylbenzene hydroperoxide; a peroxy acid, for example, peracetic acid, trichloroperacetic acid, trifluoroperacetic acid, perbenzoic acid, and p-nitroperbenzoic acid; and Oxone, for example, a potassium salt of persulfuric acid (potassium peroxymonosulfate). These co-oxidants may also be used alone or in combination. As the co-oxidant, practically used may be the peroxide or the peroxy acid, for example, the peroxide such as tert-butyl hydroperoxide (TBHP).

The amount of the co-oxidant may be, for example, about 0.1 to 100 mol (e.g., about 1 to 50 mol), preferably about 1.5 to 30 mol, and more preferably about 5 to 25 mol (e.g., about 5 to 15 mol), relative to 1 mol of the compound represented by the formula (2).

The oxidation reaction may be carried out in the coexistence of a coexisting substance (for example, an acid, a base, and a salt). The reaction in the presence of such a coexisting substance may improve the yield of an object compound.

The acid may be any of an inorganic acid, an organic acid, and a Lewis acid. As examples of the inorganic acid, there may be mentioned a mineral acid such as hydrochloric acid, hydrogen chloride, hydrobromic acid, hydrogen bromide, sulfuric acid, sulfurous acid, fuming sulfuric acid, nitric acid, fuming nitric acid, nitrous acid, phosphoric acid, boric acid, hydrofluoboric acid, carbonic acid, or silicic acid.

The organic acid may include an organic carboxylic acid compound and a sulfonic acid compound. As examples of the organic carboxylic acid compound, there may be mentioned an alkanecarboxylic acid which may have a halogen atom, such as formic acid, acetic acid, trichloroacetic acid, trifluoroacetic acid, propionic acid, butyric acid, valeric acid, caproic acid, or lauric acid; a hydroxycarboxylic acid such as glycolic acid, lactic acid, malic acid, tartaric acid, or citric acid; a cycloalkanecarboxylic acid such as cyclohexanecarboxylic acid; a dicarboxylic acid or polycarboxylic acid such as oxalic acid, malonic acid, succinic acid, glutamic acid, adipic acid, fumaric acid, maleic acid, or aconitic acid; and an arenecarboxylic acid or polycarboxylic acid such as benzoic acid, phthalic acid, mellitic acid, or cinnamic acid. Examples of the sulfonic acid compound may include an alkanesulfonic acid which may have a halogen atom, such as methanesulfonic acid or trifluoromethanesulfonic acid; an arenesulfonic acid such as benzenesulfonic acid or p-toluenesulfonic acid; and a cycloalkanesulfonic acid which may be a bridged cyclic compound, such as camphorsulfonic acid.

The Lewis acid may include, for example, scandium trifluoromethanesulfonate and iron trifluoromethanesulfonate.

These acids may be used alone or in combination. A preferred acid includes a strong acid, for example, an inorganic acid such as sulfuric acid, a haloalkanecarboxylic acid such as trifluoroacetic acid, and sulfonic acid. Practically used may be sulfuric acid.

The amount of the acid (or acid catalyst) is not particularly limited to a specific one and may be, for example, about 0.0001 to 0.1 equivalents, preferably about 0.0005 to 0.05 equivalents, and more preferably 0.001 to 0.01 equivalents, relative to 1 mol of the compound represented by the formula (2).

The base may include an inorganic base and an organic base. As examples of the inorganic base, there may be mentioned an alkali metal carbonate or hydrogen carbonate such as sodium carbonate, potassium carbonate, cesium carbonate, lithium carbonate, sodium hydrogen carbonate, or potassium hydrogen carbonate; an alkali metal alkoxide such as t-butoxypotassium; an alkali metal hydroxide such as sodium hydroxide or potassium hydroxide; an alkaline earth metal hydroxide such as calcium hydroxide or barium hydroxide; a polyvalent metal hydroxide such as aluminum hydroxide; and an alkylated alkali metal such as n-butyllithium. Examples of the organic base may include a tertiary amine such as pyridine or triethylamine. These bases or salts may also be used alone or in combination. As the base, the alkali metal carbonate, for example, potassium carbonate, may practically be used.

The salt (including an inorganic halide) may include an inorganic salt, an organic acid salt, and a transition metal complex (or complex salt). As examples of the inorganic salt, there may be mentioned an inorganic acid salt, for example, a metal halide, e.g., an alkali metal halide such as sodium chloride, potassium chloride, or potassium bromide, and an alkaline earth metal halide such as calcium chloride; an alkali metal sulfate such as sodium sulfate or potassium sulfate, an alkaline earth metal sulfate such as magnesium sulfate, calcium sulfate, or barium sulfate, and a polyvalent metal sulfate such as aluminum sulfate, copper sulfate, iron sulfate, nickel sulfate, or cobalt sulfate; an alkali metal nitrate such as sodium nitrate or potassium nitrate, an alkaline earth metal nitrate such as magnesium nitrate or barium nitrate, and a polyvalent metal nitrate such as nickel nitrate. As examples of the organic acid salt, there may be mentioned a carboxylic acid salt (e.g., an acetate) such as magnesium acetate or manganese acetate. The transition metal complex (or complex salt) may include a cobalt complex. These salts may be a neutral salt.

The amount of the base or salt may be, for example, about 0.1 to 15 mol, preferably about 0.5 to 10 mol, and more preferably about 1 to 7 mol (e.g., about 2 to 6 mol), relative to 1 mol of the compound represented by the formula (2).

The coexisting substance may positively coexist with the oxidant and the co-oxidant in the reaction, and the timing for the addition of the coexisting substance to the reaction system is not particularly limited to specific manner. The coexisting substance may be added to the reaction system in advance before the addition of the oxidant and the co-oxidant or may be added after the addition of the oxidant and the co-oxidant.

The reaction may be carried out in a solvent. The solvent may include various solvents (particularly, a solvent inert or inactive to the reaction), for example, an ether-series solvent (e.g., a chain ether compound such as dimethyl ether, diethyl ether, diisopropyl ether, methyl tert-butyl ether, dimethoxyethane, or cyclopentyl methyl ether, and a cyclic ether compound such as tetrahydrofuran or dioxane), a hydrocarbon-series solvent [e.g., an aromatic hydrocarbon-series solvent (such as benzene, toluene, xylene, or chlorobenzene) and an aliphatic hydrocarbon-series solvent (such as pentane, hexane, heptane, or octane)], an amide-series solvent (such as N,N-dimethylformamide, N,N-dimethylacetamide, or N-methylpyrrolidone), an alcoholic solvent (e.g., an alkanol such as methanol, trichloromethanol, trifluoromethanol, ethanol, trifluoroethanol, trichloroethanol, n-propanol, 2-propanol, n-butanol, s-butanol, t-butanol, pentanol, or hexanol; a cycloalkanol such as cyclopropanol, cyclobutanol, cyclopentanol, or cyclohexanol; a diol such as ethylene glycol, 1,3-propanediol, 1,4-butanediol, or 1,5-pentanediol; and a polyhydric alcohol such as glycerin), an ester-series solvent (such as methyl acetate, ethyl acetate, or isopropyl acetate), a nitrile-series solvent (such as acetonitrile, propionitrile, or benzonitrile), a nitroalkane-series solvent (nitromethane, nitroethane), and a basic nitrogen-containing solvent (a tertiary amine, for example, a trialkylamine such as triethylamine, and a cyclic amine such as pyridine or quinoline). These solvents may be used alone or as a mixed solvent. A preferred solvent may be a mixed solvent containing at least two kinds of organic solvents, for example, a mixed solvent of 2,2,2-trifluoroethanol and chlorobenzene.

The reaction may be carried out at a temperature of about −50° C. to 50° C. (for example, about −30° C. to 0° C.), and the atmosphere may be, for example, an oxygen-containing atmosphere (e.g., in air) or an inert atmosphere. Moreover, the reaction may usually be carried out while continuously or intermittently adding a strong oxidant to the reaction system.

The reaction in the presence of the base or the salt may also be carried out at a temperature of about −50° C. to 50° C. (for example, about −30° C. to 0° C.) as described above.

After the completion of the reaction, the reaction mixture may be separated and purified by a usual separation and purification means, for example, a method such as solvent extraction, neutralization, concentration, washing, crystallization, or recrystallization, to give an object compound with a high yield.

Incidentally, the Nonpatent Document 2 discloses the oxidation reaction of a substrate such as acetyloxycyclopentane with the oxidant and the co-oxidant in the presence of the acid. However, in the Nonpatent Document 2, an object compound is only obtained with a low yield. In contrast, according to the present invention, oxidizing the compound having the specific substituent at the 7-position of the steroid skeleton can selectively or specifically introduce an oxo group on the 15-position of the steroid skeleton, while maintaining an optical activity for an optically active substance, and can produce an object compound with high conversion and selectivity.

EXAMPLES

The following examples are intended to describe this invention in further detail and should by no means be interpreted as defining the scope of the invention.

Example 1

[Chem. 8]

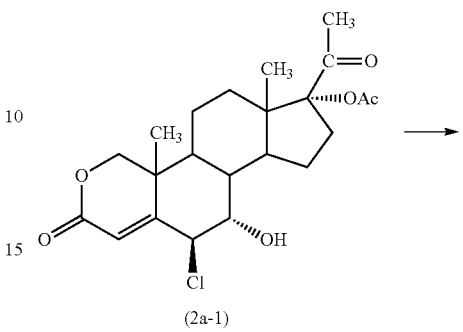

The above compound (2a-1) was subjected to an oxidation reaction to give the above compound (1a-1).

Specifically, a mixture of 6β-chloro-7α-hydroxy-3,20-dioxo-2-oxapregn-4-en-17-yl acetate (the above compound (2a-1), 90.0 g), 2,2,2-trifluoroethanol (162 mL), and chlorobenzene (2.520 L) was cooled to −24±2° C., and iodobenzene diacetate (409.2 g) and sulfuric acid (0.3 mL) was added thereto. To the resultant mixture was added dropwise a tert-butyl hydroperoxide aqueous solution (301 mL) having a concentration of 70% at the same temperature, and the resulting mixture was stirred for 40 minutes while maintaining the above temperature. To the reaction mixture was added potassium carbonate (131.8 g) while maintaining the above temperature, and the resulting mixture was stirred for 44 hours at the same temperature.

The resulting reaction mixture was poured into a cooled solution containing sodium pyrosulfite (90.0 g) and sodium chloride (540.0 g) in water (1.53 L) and having a temperature of 2° C., the reaction vessel was washed with ethyl acetate (720 mL), and the combined mixture was stirred at a room temperature. The resulting mixture was separated into an upper layer (or phase) and a lower layer (or phase), and the lower layer was re-extracted with ethyl acetate (360 mL). These upper layers were combined, and the combined upper layers were washed with a solution containing sodium dihydrogen phosphate (180.0 g) and sodium chloride (270.0 g) in water (1.8 L) and having a pH of 7.5 adjusted with sodium hydroxide having a concentration of 30% by weight. Then, the resulting organic layer was washed with a solution containing sodium chloride (225.0 g) in water (720 ml), and the washed layer was concentrated at a temperature of not higher than 50° C. under a reduced pressure until the remaining amount was reduced to about 2.52 L. The concentrate was stirred vigorously, and heptane (5.4 L) was added thereto. The resulting mixture was stirred at 18° C. overnight. The precipitated crystal was collected by filtration and was washed with heptane (315 mL). The resulting crude crystal was dissolved in a mixture of acetone (378 mL) and water (38 mL), and water (1.44 L) was added thereto with vigorous stirring. The resulting suspension was concentrated at a temperature of not higher than 50° C. under a reduced pressure until the remaining amount was reduced to about 1.44 L. The suspension was stirred for 75 minutes at 10° C., and the crystal was collected by filtration and was washed with water (270 mL). The resulting crystal was dried at 50° C. for 10 hours to give 6β-chloro-7α-hydroxy-3,15,20-trioxo-2-oxapregn-4-en-17-yl acetate (the above compound (1a-1), 65.2 g (70.1% yield)). The compound was purified by column chromatography (elution solvent n-hexane:ethyl acetate=1:1 to 1:2) to obtain an analytical sample.

NMR: $^1$H-NMR (400 MHz, CDCl$_3$) δ 0.83 (3H, s), 1.48 (3H, s), 1.49-1.71 (4H, m), 2.12-2.22 (1H, m), 2.14 (3H, s), 2.19 (3H, s), 2.46-2.56 (2H, m), 2.78 (1H, d, J=11.2 Hz), 3.49 (1H, d, J=20.0 Hz), 4.09, 4.22 (2H, ABq, J=10.8 Hz), 4.47 (1H, d, J=2.9 Hz), 5.04 (1H, brs), 6.01 (1H, s)

MASS: m/z 438 (M$^+$)

Example 2

[Chem. 9]

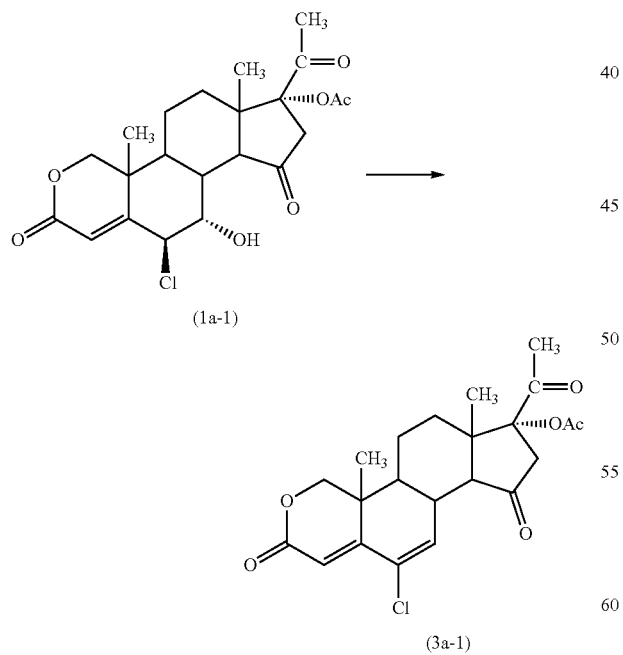

The above compound (1a-1) was subjected to a dehydration reaction to give the above compound (3a-1).

Specifically, a mixture of 6β-chloro-7α-hydroxy-3,15,20-trioxo-2-oxapregn-4-en-17-yl acetate (the above compound (1a-1), 9.35 g) and dichloromethane (240 ml) was cooled with ice under an argon atmosphere, and to the mixture was added dropwise a solution of Martin sulfurane (bis[α,α-bis(trifluoromethyl)benzenemethanolato]diphenylsulfur) (20 g) in dichloromethane (110 ml). The resulting mixture was stirred at a room temperature overnight.

The reaction mixture was concentrated under a reduced pressure. The resulting concentrate was purified by column chromatography (elution solvent n-hexane:ethyl acetate=1:1 to 2:3) to give 17α-acetoxy-6-chloro-2-oxa-4,6-pregnadiene-3,15,20-trione (the above compound (3a-1), 5.8 g (64.7% yield)).

Comparative Example

In accordance with Chart 2 and the conditions of each reaction step described in the Nonpatent Document 1, Compound 12 was prepared from Compound 8 as a starting material via Compound 9 and Compound 10. The yield was 7.8%. Furthermore, Compound 16 was prepared from Compound 12 via Compound 13, Compound 14, and Compound 15a. The yield was 7.7%.

INDUSTRIAL APPLICABILITY

The 15-oxosteroid compound of the present invention represented by the formula (1) can produce the compound having the oxo group on the 15-position of the steroid skeleton by the elimination of the group —OR$_6$. Thus, the compound of the present invention is useful as an intermediate for producing the compound having a high pharmacological activity (for example, an antiandrogenic activity).

The invention claimed is:

1. A 15-oxosteroid compound represented by the following formula (1):

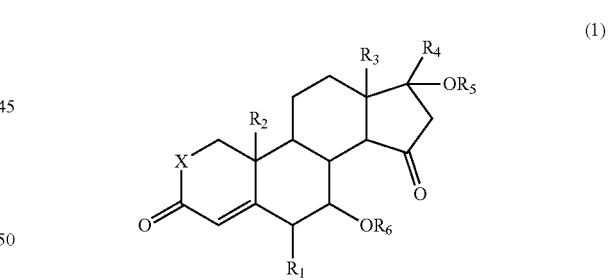

wherein R$_1$, R$_2$, and R$_3$ are the same or different and each represent a halogen atom, an alkyl group, a haloalkyl group, an alkoxy group, or a haloalkoxy group, R$_4$ represents a hydrogen atom, a halogen atom, an alkyl group, an alkoxy group, an acyl group, or an alkoxycarbonyl group, R$_5$ represents a hydrogen atom, an alkyl group, or an acyl group, R$_6$ represents a hydrogen atom, an alkyl group, an acyl group, or a sulfonyl group, and X represents an oxygen atom (O) or a methylene group (CH$_2$).

2. The 15-oxosteroid compound according to claim 1, which is represented by the following formula (1a):

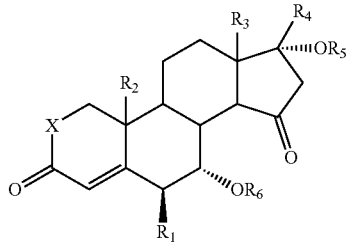

(1a)

wherein $R_1$, $R_2$, $R_3$, $R_4$, $R_5$, $R_6$, and X have the same meanings as defined in claim 1.

3. The 15-oxosteroid compound according to claim 1, wherein $R_1$ is a halogen atom, $R_2$ and $R_3$ are the same or different and are an alkyl group or a haloalkyl group, $R_4$ and $R_5$ are the same or a different acyl group, $R_6$ is a hydrogen atom, an acyl group, or a sulfonyl group, and X is an oxygen atom.

4. A process for producing a 15-oxosteroid compound recited in claim 1, the process comprising oxidizing a compound represented by the following formula (2):

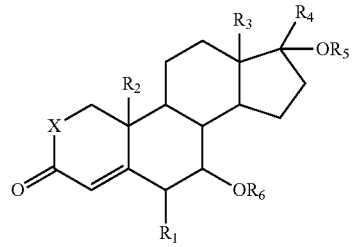

(2)

wherein $R_1$, $R_2$, $R_3$, $R_4$, $R_5$, $R_6$, and X have the same meanings as defined in claim 1 with an oxidant and a co-oxidant.

5. The process according to claim 4, wherein a coexisting substance is added in the oxidation with the oxidant and the co-oxidant.

6. The process according to claim 4, wherein the oxidant contains a hypervalent iodine compound, and the co-oxidant contains a peroxide and/or a peroxy acid.

7. The process according to claim 4, wherein the compound is allowed to react with a hypervalent iodine compound and a peroxide in the presence of a strong acid in a solvent, then an alkali metal carbonate is added to the reaction system and the reaction is continued.

* * * * *